(12) United States Patent
Scribner et al.

(10) Patent No.: US 6,979,341 B2
(45) Date of Patent: *Dec. 27, 2005

(54) EXPANDABLE PREFORMED STRUCTURES FOR DEPLOYMENT IN INTERIOR BODY REGIONS

(75) Inventors: Robert M Scribner, Los Altos, CA (US); Karen D Talmadge, Palo Alto, CA (US)

(73) Assignee: Kyphon Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/837,350

(22) Filed: Apr. 18, 2001

(65) Prior Publication Data

Related U.S. Application Data

(63) Continuation of application No. 09/088,459, filed on Jun. 1, 1998, now abandoned, and a continuation-in-part of application No. 08/788,786, filed on Jan. 23, 1997, now Pat. No. 6,235,043, which is a continuation of application No. 08/188,224, filed on Jan. 26, 1994, now abandoned.

(51) Int. Cl.[7] ............................................ A61M 29/00
(52) U.S. Cl. ..................... 606/192; 606/61; 623/17.11; 623/23.67
(58) Field of Search ................. 606/192, 193, 606/194, 195, 60, 61, 191; 623/17.11, 17.12, 623/23.11, 23.67; 604/95, 96, 95.03, 96.01

(56) References Cited

U.S. PATENT DOCUMENTS

| | | | |
|---|---|---|---|
| 2,849,002 A | 8/1958 | Oddo | |
| 3,045,677 A * | 7/1962 | Wallace | 604/101.05 |
| 3,154,077 A | 10/1964 | Cannon | |
| 3,640,282 A | 2/1972 | Kamen et al. | |
| 3,648,294 A * | 3/1972 | Shahrestani | 623/23.42 |
| 3,779,239 A | 12/1973 | Fischer et al. | |
| 3,850,176 A * | 11/1974 | Gottschalk | 604/907 |
| 3,889,685 A | 6/1975 | Miller Jr. et al. | |
| 4,261,339 A | 4/1981 | Hanson et al. | |
| 4,292,974 A | 10/1981 | Fogarty et al. | |
| 4,327,736 A | 5/1982 | Inoue | |
| 4,338,942 A | 7/1982 | Fogarty | |
| 4,402,307 A | 9/1983 | Hanson et al. | |
| 4,467,790 A | 8/1984 | Schiff | |
| 4,531,512 A | 7/1985 | Wolvek et al. | |
| 4,848,344 A | 7/1989 | Sos et al. | |
| 4,917,088 A | 4/1990 | Crittenden | |
| 4,969,888 A | 11/1990 | Scholten et al. | |
| 4,983,167 A | 1/1991 | Sahota | |
| 5,102,390 A | 4/1992 | Crittenden et al. | |
| 5,104,376 A | 4/1992 | Crittenden | |
| 5,108,404 A | 4/1992 | Scholten et al. | |
| 5,163,989 A * | 11/1992 | Campbell et al. | 65/110 |
| 5,295,994 A * | 3/1994 | Bonutti | 604/103 |

(Continued)

FOREIGN PATENT DOCUMENTS

EP        0 566 684        6/1987

(Continued)

Primary Examiner—Henry Bennett
Assistant Examiner—Andrea M. Ragonese
(74) Attorney, Agent, or Firm—Ryan Kromholz & Manion, S.C.

(57) ABSTRACT

An expandable structure made from an elastomer material is preformed to a desired geometry by exposure to heat and pressure. The structure undergoes controlled expansion and further distention in cancellous bone, with controlled deformation and without stress failure.

15 Claims, 10 Drawing Sheets

U.S. PATENT DOCUMENTS

| | | | |
|---|---|---|---|
| 5,352,199 A * | 10/1994 | Tower .................. | 604/103.07 |
| 5,415,635 A | 5/1995 | Bagaoisan et al. | |
| 5,500,181 A * | 3/1996 | Wang et al. ................ | 264/532 |
| 5,587,125 A | 12/1996 | Roychowdhury | |
| 5,741,282 A | 4/1998 | Anspach, III et al. | |
| 5,766,151 A | 6/1998 | Valley et al. | |
| 5,827,289 A | 10/1998 | Reiley et al. | |
| 5,843,116 A * | 12/1998 | Crocker et al. ............. | 606/192 |
| 5,938,582 A | 8/1999 | Ciamacco, Jr. et al. | |
| 5,972,015 A | 10/1999 | Scribner et al. | |
| 6,048,346 A | 4/2000 | Reiley et al. | |
| 6,066,154 A | 5/2000 | Reiley et al. | |
| D439,980 S | 4/2001 | Reiley et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,379,373 B1 * | 4/2002 | Sawhney et al. ........... | 606/193 |
| 6,383,212 B2 * | 5/2002 | Durcan et al. .............. | 606/108 |
| 6,607,544 B1 * | 8/2003 | Boucher et al. ............ | 606/192 |

FOREIGN PATENT DOCUMENTS

| | | | | | |
|---|---|---|---|---|---|
| EP | 0 274 411 | 7/1988 | | | |
| EP | 0 597 465 | 9/1988 | | | |
| EP | 0 135 990 | 9/1990 | | | |
| EP | 0 410 072 | 1/1991 | | | |
| EP | 0 436 501 | 4/1993 | | | |
| EP | 0 420 488 | 7/1993 | | | |
| EP | 0 439 202 | 9/1993 | | | |
| EP | 0 592 885 | 9/1993 | | | |
| EP | 0 318 919 | 1/1994 | | | |
| EP | 0 383 794 | 6/1994 | | | |
| EP | 0 355 937 | 11/1995 | | | |
| EP | 0 713 712 | 5/1996 | | | |
| EP | 0 730 879 | 9/1996 | | | |
| EP | 0 531 117 | 1/1997 | | | |
| EP | 0 362 826 | 5/1997 | | | |
| EP | 0 779 062 | 6/1997 | | | |
| EP | 0 826 395 | 3/1998 | | | |
| EP | 0 834 293 | 4/1998 | | | |
| WO | WO 89/02763 | 4/1989 | | | |
| WO | WO91/17788 | 11/1991 | | | |
| WO | WO 92/11892 | 7/1992 | | | |
| WO | WO92/19440 | 11/1992 | | | |
| WO | WO94/02197 | 2/1994 | | | |
| WO | WO95/20362 | 8/1995 | | | |
| WO | WO95/22367 | 8/1995 | | | |
| WO | WO 9520362 A1 * | 8/1995 | .......... | A61B 17/68 | |
| WO | WO96/04951 | 2/1996 | | | |
| WO | WO96/12516 | 5/1996 | | | |
| WO | WO96/39970 | 12/1996 | | | |
| WO | WO97/03716 | 2/1997 | | | |
| WO | WO97/17098 | 5/1997 | | | |
| WO | WO97/17099 | 5/1997 | | | |
| WO | WO97/40877 | 11/1997 | | | |
| WO | WO98/03218 | 1/1998 | | | |
| WO | WO 9856301 A1 * | 12/1998 | .......... | A61B 17/56 | |
| WO | WO 99/29246 | 6/1999 | | | |
| WO | WO 99/37212 | 7/1999 | | | |
| WO | WO 99/51149 | 10/1999 | | | |
| WO | WO 99/62416 | 12/1999 | | | |
| WO | WO 01/28439 | 4/2001 | | | |
| WO | WO 01/76514 | 10/2001 | | | |

* cited by examiner

EXPANDABLE PREFORMED STRUCTURES FOR DEPLOYMENT IN INTERIOR BODY REGIONS

This application is a continuation of application Ser. No. 09/088,459, filed Jun. 1, 1998 (now abandoned). This application is also a continuation-in-part of application Ser. No. 08/788,786, filed Jan. 23, 1997 (now U.S. Pat. No. 6,235,043), which is a continuation of application Ser. No. 08/188,224, filed Jan. 26, 1994 (now abandoned).

FIELD OF THE INVENTION

The invention relates to expandable structures, which, in use, are deployed in interior body regions of humans and other animals.

BACKGROUND OF THE INVENTION

The deployment of expandable structures, generically called "balloons," into cancellous bone is known. For example, U.S. Pat. Nos. 4,969,888 and 5,108,404 disclose apparatus and methods using expandable structures in cancellous bone for the fixation of fractures or other osteoporotic and non-osteoporotic conditions of human and animal bones.

SUMMARY OF THE INVENTION

When deployed in cancellous bone, expandable structures should undergo expansion and distention without failure. Furthermore, such structures, when distended, should generally match the geometry of the interior bone space in which the structure is deployed. In addition, such structures should allow preferential expansion to areas of lowest bone density. Exposure to cancellous bone also requires materials that exhibit superior resistance to surface abrasion and tensile stresses.

It is has been discovered that expandable structures made from an elastomer material, e.g., polyurethane, which have been preformed to a desired shape, e.g., by exposure to heat and pressure, can undergo controlled expansion and further distention in cancellous bone, without failure, while exhibiting superior resistance to surface abrasion and puncture when contacting cancellous bone.

Features and advantages of the inventions are set forth in the following Description and Drawings, as well as in the appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The preferred embodiment describes improved systems and methods that embody features of the invention in the context of treating bones. This is because the new systems and methods are advantageous when used for this purpose. However, aspects of the invention can be advantageously applied for diagnostic or therapeutic purposes in other areas of the body.

The new systems and methods will be more specifically described in the context of the treatment of human vertebra. Of course, other human or animal bone types can be treated in the same or equivalent fashion.

Figure 1:
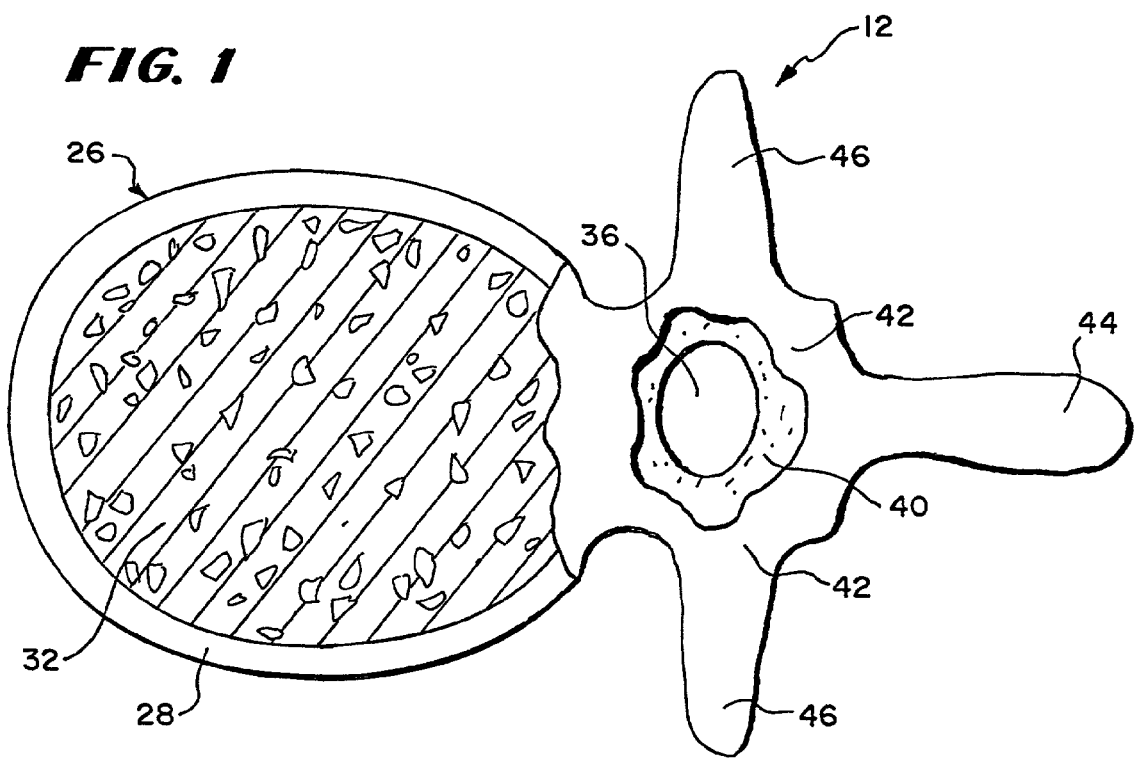
FIG. 1 is a coronal view of a vertebral body.
Figure 2:
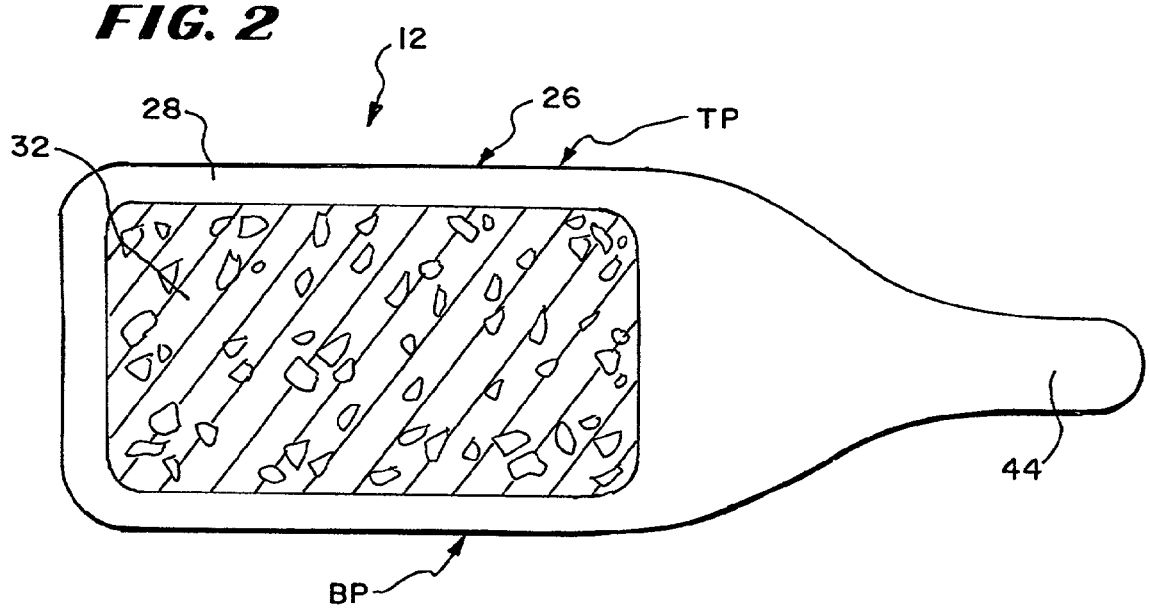
FIG. 2 is a lateral view of the vertebral body shown in FIG. 1.

FIG. 1 shows a coronal (top) view of a human lumbar vertebra 12. FIG. 2 shows a lateral (side) view of the vertebra. The vertebra 12 includes a vertebral body 26, which extends on the anterior (i.e., front or chest) side of the vertebra 12. The vertebral body 26 is shaped generally like a marshmallow.

As FIGS. 1 and 2 show, the vertebral body 26 includes an exterior formed from compact cortical bone 28. The cortical bone 28 encloses an interior volume of reticulated cancellous, or spongy, bone 32 (also called medullary bone or trabecular bone).

The spinal canal 36 (see FIG. 1), is located on the posterior (i.e., back) side of each vertebra 12. The spinal cord (not shown) passes through the spinal canal 36. The vertebral arch 40 surrounds the spinal canal 36. Left and right pedicles 42 of the vertebral arch 40 adjoin the vertebral body 26. The spinous process 44 extends from the posterior of the vertebral arch 40, as do the left and right transverse processes 46.

It may be indicated, due to disease or trauma, to compress cancellous bone within the vertebral body. The compression, for example, can be used to form an interior cavity, which receives a filling material, e.g., a flowable material that sets to a hardened condition, like bone cement, allograft tissue, autograft tissue, hydroxyapatite, or synthetic bone substitute, as well as a medication, or combinations thereof, to provide improved interior support for cortical bone or other therapeutic functions, or both. The compaction of cancellous bone also exerts interior force upon cortical bone, making it possible to elevate or push broken and compressed bone back to or near its original prefracture, or other desired, condition.

I. Preformed Expandable Structures

Figure 3:
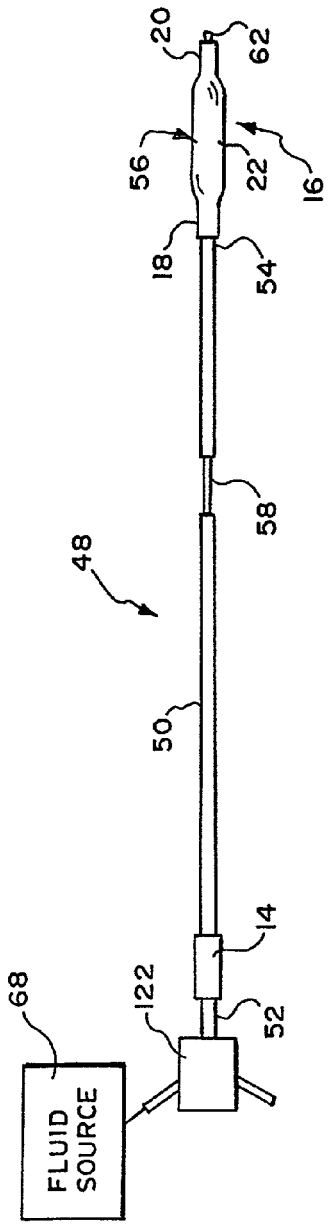
FIG. 3 is a plan view of a tool which carries at its distal end an expandable structure that embodies features of the invention.

FIG. 3 shows a tool 48 for accessing bone for the purpose of compacting cancellous bone. The tool 48 includes a catheter tube 50 having a proximal end 52 and a distal end 54. The proximal end 52 carries a handle 14 to facilitate gripping and maneuvering the tube 50. The proximal end 52 also carries a fitting 122 to enable connection of the tool 48 to external equipment, as will be described later. The distal end 54 of the tool 48 carries a structure 56, which, in use, is intended to be expanded in cancellous bone, e.g., in the vertebral body 26 shown in FIGS. 1 and 2.

A. Desired Physical and Mechanical Properties

The material from which the structure 56 is made should possess various physical and mechanical properties to optimize its functional capabilities to compact cancellous bone. The three most important properties are the ability to expand its volume; the ability to deform in a desired way when expanding and assume a desired shape inside bone; and the ability to withstand abrasion, tearing, and puncture when in contact with cancellous bone.

1. Expansion Property

A first desired property for the structure material is the ability to expand or otherwise increase its volume without failure. This property enables the structure 56 to be deployed in a collapsed, low profile condition subcutaneously, e.g., through a cannula, into the targeted bone region. This property also enables the expansion of the structure 56 inside the targeted bone region to press against and compress surrounding cancellous bone, or move cortical bone to a prefracture or other desired condition, or both.

The expansion property for the material can be characterized, e.g., by ultimate elongation properties, which indicate the greatest degree of expansion that the material can accommodate prior to failure. An ultimate elongation of at least about 300% before material failure provides the ability to expand to the volume necessary to compact cancellous bone, as well as lift contiguous cortical bone. A material with an ultimate elongation of less than about 300% is prone to exhibit failure at inflation volumes short of the desired bone compacting volume.

2. Shape Property

A second desired property for the material of the structure 56 is the ability to predictably deform during expansion, so that the structure 56 consistently achieves a desired shape inside bone.

The shape of the structure 56, when expanded in bone, is selected by the physician, taking into account the morphology and geometry of the site to be treated. The shape of the cancellous bone to be compressed, and the local structures that could be harmed if bone were moved inappropriately, are generally understood by medical professionals using textbooks of human skeletal anatomy along with their knowledge of the site and its disease or injury, and also taking into account the teachings of U.S. patent application Ser. No. 08/788,786, filed Jan. 23, 1997, and entitled "Improved Inflatable Device for Use in Surgical Protocol Relating to Fixation of Bone," which is incorporated herein by reference. The physician is also able to select the desired expanded shape inside bone based upon prior analysis of the morphology of the targeted bone using, for example, plain film x-ray, fluoroscopic x-ray, or MRI or CT scanning. The expanded shape inside bone is selected to optimize the formation of a cavity that, when filled with a selected material, provides support across the region of the bone being treated. The selected expanded shape is made by evaluation of the predicted deformation that will occur with increased volume due to the shape and physiology of the targeted bone region.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure 56 results in a worsening of the overall condition of the bone and surrounding anatomic structures, for example, by injury to surrounding tissue or causing a permanent adverse change in bone biomechanics.

As one general consideration, in cases where the bone disease causing fracture (or the risk of fracture) is the loss of cancellous bone mass (as in osteoporosis), the selection of the expanded shape of the structure 56 inside bone should take into account the cancellous bone volume which should be compacted to achieve the desired therapeutic result. An exemplary range is about 30% to 90% of the cancellous bone volume, but the range can vary depending upon the targeted bone region. Generally speaking, compacting less of the cancellous bone volume leaves more uncompacted, diseased cancellous bone at the treatment site.

Another general guideline for the selection of the expanded shape of the structure 56 inside bone is the amount that the targeted fractured bone region has been displaced or depressed. The controlled deformation diameter expansion of the structure 56 within the cancellous bone region inside a bone can elevate or push the fractured cortical wall back to or near its anatomic position occupied before fracture occurred. Generally speaking, inadequate compaction of cancellous bone results in less lifting of contiguous cortical bone.

For practical reasons, it is desired that the expanded shape of the structure 56 inside bone, when in contact with cancellous bone, substantially conforms to the shape of the structure 56 outside bone, when in an open air environment. This allows the physician to select in an open air environment a structure having an expanded shape desired to meet the targeted therapeutic result, with the confidence that the expanded shape inside bone will be similar in important respects.

An optimal degree of shaping can be achieved by material selection and by special manufacturing techniques, e.g., thermoforming or blow molding, as will be described in greater detail later.

3. Toughness Property

A third desired property for the material of the structure 56 is the ability to resist surface abrasion, tearing, and puncture when in contact with cancellous bone.

This property can be characterized in various ways. For example, a Taber Abrasion Resistance Value of less than about 90 mg loss indicates resistance to puncture when contacting cancellous bone. A Rotating Drum Abrasion Resistance Value of less than 70 mm$^3$ also indicates resistance to puncture when contacting cancellous bone. This property can further be characterized, e.g., by an Elmendorf tear strength of greater than about 280 lbf/in, which indicates resistance to failure caused by cancellous bone abrasion. This property can also be characterized, e.g., by a Shore Hardness value of less than about 100 A. This value indicates a degree of elasticity, flexibility, and ductility.

Materials with a Taber Abrasion Resistance Value greater than about 90 mg loss, or a Rotating Drum Abrasion Resistance Value greater than about 70 mm$^3$, or an Elmendorf tear strength value of less than about 280 lbf/in, or a Shore Hardness value greater than about 100 A are not well suited for expansion in cancellous bone, because failure may occur prior to expansion to the desired diameter.

B. Enhanced Expansion and Shape Properties

The expansion and shape properties just described can be enhanced and further optimized for compacting cancellous bone by selecting an elastomer material, which also possess the capability of being preformed, i.e., to acquire a desired shape by exposure, e.g., to heat and pressure, e.g., through the use of conventional thermoforming or blow molding techniques. Candidate materials that meet this criteria include polyurethane, silicone, thermoplastic rubber, nylon, and thermoplastic elastomer materials. In a most preferred embodiment, polyurethane material is used.

1. Single Preformed Expandable Structures

Figure 4A:
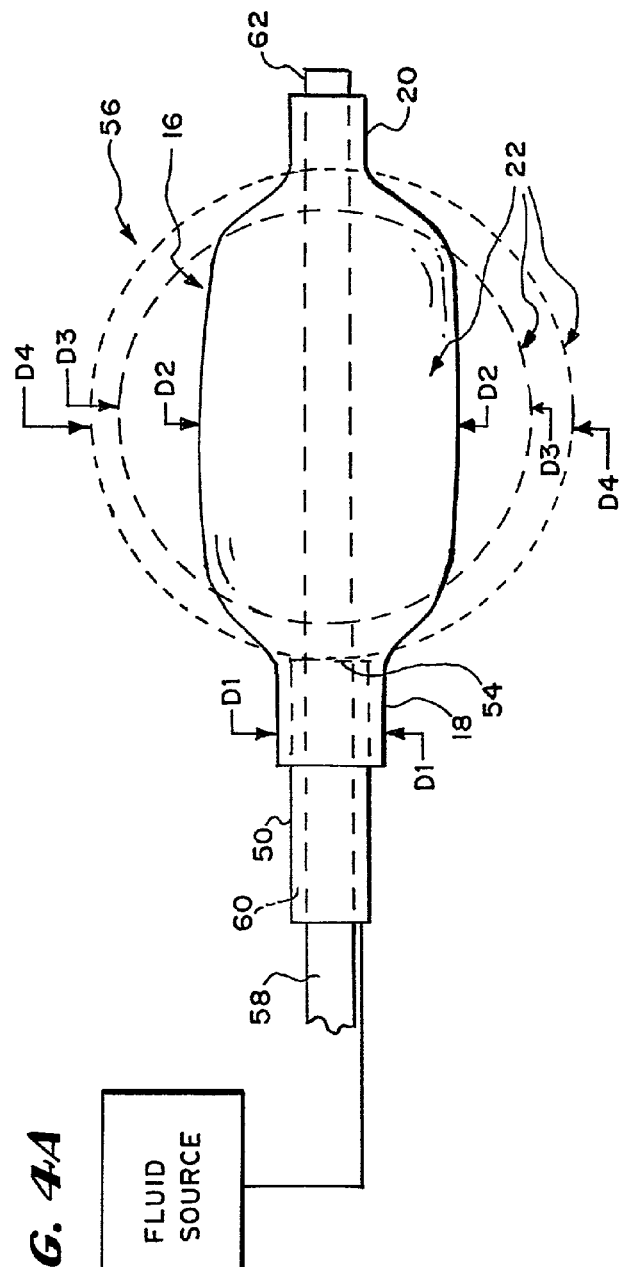
FIGS. 4A and 4B are enlarged side views of the expandable structure carried by the tool shown in FIG. 3.

In the embodiment shown in FIG. 4A, the structure 56 comprises an elongated tube 16 made from a polyurethane material. The tube 16 possesses end regions 18 and 20, each having a first diameter (designated D1 in FIG. 4A). The tube 16 further includes an intermediate preformed region 22. The diameter of the preformed intermediate region 22 has been enlarged by exposure to heat and pressure to a normally expanded shape having an enlarged diameter (designated D3 in FIG. 4A) greater than the first diameter D1. The normally expanded shape D3 exists in an open air environment, prior to placement inside an interior body region.

Figure 5:
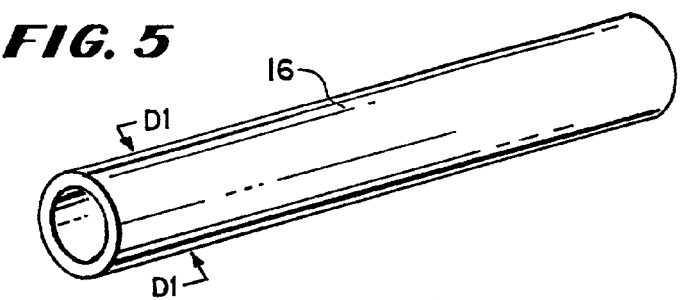
FIG. 5 is a perspective end view of a tube made of a polyurethane or elastomer material prior to being formed into the expandable structure shown in FIG. 4A.
Figure 6:
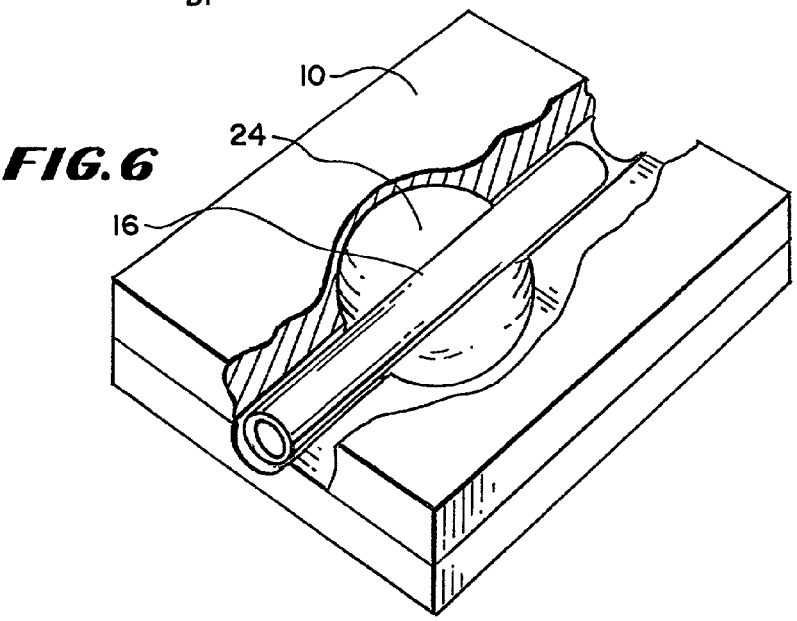
FIG. 6 is a top perspective view of the tube shown in FIG. 5 positioned in a shape-forming fixture, of which parts are broken away to permit viewing its interior.
Figure 7:
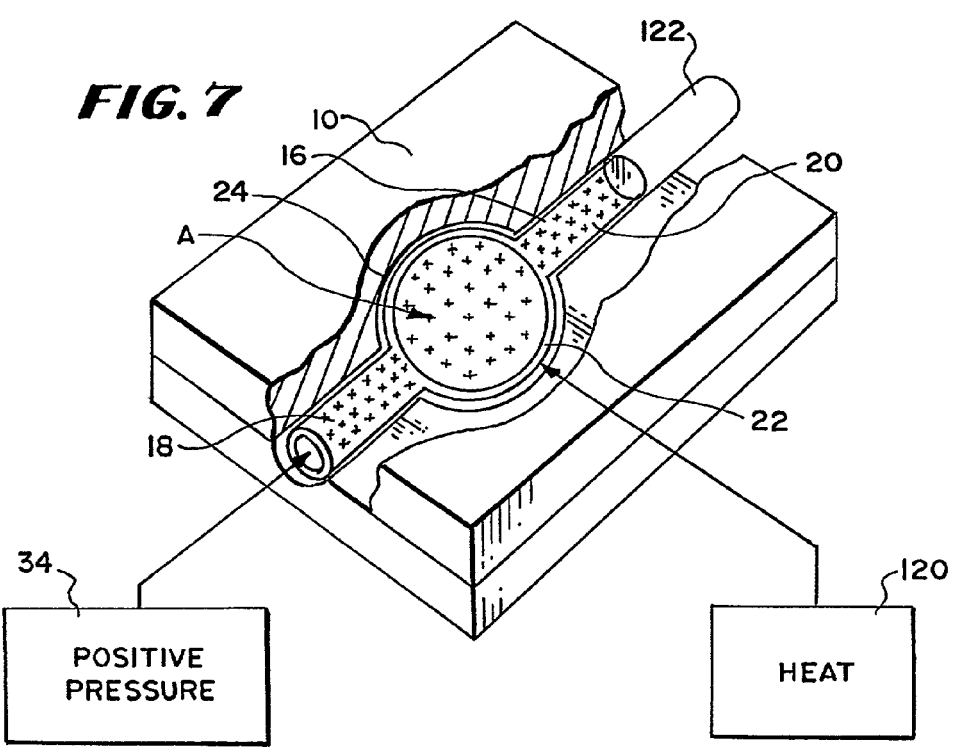
FIG. 7 is a top perspective view of the shape-forming fixture shown in FIG. 6, in use applying heat and pressure to a region of the tube to form a shaped, expandable region.

As FIG. 5 shows, the tube 16 is initially formed from polyurethane (or another preferred) material, for example, by standard polymer extrusion and molding processes. As FIGS. 6 and 7 show, the shaped region 22 is created by exposing the region 22 to heat within a fixture or mold 10, while positive interior pressure is applied to the tube 16 within the region 22. The fixture 10 includes a cavity 24, in which the region 22 rests while heat and pressure are applied. The cavity 24 has a geometry that the region 22 is intended to assume when inflated with interior pressure in the fixture 10. In the illustrated embodiment, a generally spherical shape is envisioned.

The heat can be applied by coupling the cavity 24 to a source 120 of heat energy of the fixture 10 itself (as FIG. 7 shows), or conveying a hot air stream or the equivalent into the cavity 24. The temperature selected is that at which the tube material will soften and form.

The range of temperatures in which softening occurs will depend upon the particular composition of the polymeric material used. For example, for polyurethane, the softening temperature lays in the range of about 50° C. to about 190° C. An operating range of softening temperatures for a given plastic material can be empirically determined.

As FIG. 7 shows, while in a heat-softened state and confined within the cavity 24, one end region 18 is coupled to a source 34 of pressurized fluid. The other end region 20 not coupled to the source 34 is closed with a cap 122 or otherwise blocked to retain pressurized fluid in the tube 16. Preferably, the pressurized fluid is air or an inert gas, designated A in FIG. 7.

The magnitude of pressure will vary depending upon the wall thickness and other physical characteristics of the elastomer material used. The pressure must be less than the burst strength of the tube material. Typically, air pressure in the range of 5 to 1000 psi can be used.

The introduction of pressurized air A into the tube 16 causes the heat-softened region 22 to expand or billow outwardly in the cavity 24, as FIG. 7 shows. The cavity 24 limits the extent to which the heat-softened region 22 can expand. The region 22 will, upon expansion, conform to the geometry of the cavity 24. The extension of the heat-softened material in the cavity 24 uniformly relieves material stress in the region 22, as the region 22 acquires a new expanded shape, having the enlarged diameter D3 shown in FIG. 4A.

The application of heat is terminated, and the region 22 is allowed to cool, while pressurized fluid is applied to maintain the enlarged diameter D3. The region 22 can be cooled by an ambient external air flow, or by a pressurized stream of cooling air. Alternatively, the cavity 24 can include interior passages through which a cooling fluid can be circulated. The speed at which cooling occurs affects the time of the overall process.

After cooling, the application of pressurized fluid is terminated. The now preformed structure 56 is removed from the cavity 24.

The normally expanded shape characteristics of the structure 56 can be achieved by other techniques. For example, the structure 56 can be formed by dipping, lost wax casting, or injection molding.

Upon removal from the fixture 10, the structure 56 is secured to the distal end 54 of the catheter tube 50. The structure of the catheter tube 50 can vary and is not critical to the invention per se. The materials for the catheter tube 50 are selected to facilitate advancement of the structure 56 into an interior body region. The catheter tube 50 can be constructed, for example, using standard flexible, medical grade plastic materials, like vinyl, nylon, polyethylenes, ionomer, polyurethane, and polyethylene tetraphthalate (PET). The catheter tube 50 can also include more rigid materials to impart greater stiffness and thereby aid in its manipulation. More rigid materials that can be used for this purpose include Kevlar™ material, PEBAX™ material, stainless steel, nickel-titanium alloys (Nitinol™ material), and other metal alloys.

In the illustrated embodiment (as best shown in FIG. 4A), the catheter tube 50 includes an interior bore 60, in which an auxiliary tube 58 is secured. It should be appreciated that the catheter tube 50 can have more than a single interior lumen, and can, e.g., have an array of multiple lumens. In the illustrated embodiment, The auxiliary tube 58 extends through the interior bore 60 and beyond the distal end 54 of the catheter tube 50. One end region 18 of the tube 16 is secured to the distal end 54 of the catheter tube 50, while the other end region 20 is secured to the free extended end 62 of the auxiliary tube 58. The end regions 18 and 20 can be secured, e.g., using adhesive or thermal bonding processes.

By drawing a vacuum (i.e., negative pressure) inside the structure 56, resident air volume is removed, and the diameter of the region 22 is diminished from its normally expanded shape D3 to a substantially collapsed, and not inflated diameter D2. The collapsed diameter D2 is, due to forming during the heat and pressure shaping process, still different than the extruded or molded diameter D1. When substantially collapsed or not inflated, the structure 56 exhibits a low profile, ideal for insertion into the targeted cancellous bone region. The low profile can be further reduced to aid insertion, if desired, by enclosing the structure 56 within a constricted introducing sleeve, or by coating the structure 56 with a lubricious material, such as silicone, or both.

As FIGS. 3 and 4 show, the interior bore 60 of the catheter tube 50 can be coupled (via the fitting 122) to a source 68 of fluid, for example, sterile saline, or a radiopaque contrast medium, which permits x-ray visualization of the structure 56. The interior bore 60 conveys the fluid into the region 22. The increase of volume within the region up to a given threshold amount (designated V(D3) in FIG. 10) will return the intermediate region 22 from the collapsed diameter D2 to the normal (i.e., enlarged, but not distended) geometry, having the shape and diameter D3.

When in its normally enlarged shape D3, the material of the structure 56 in the region 22 is not significantly stretched or stressed, because it has been previously expanded in a stress-relieved condition into this geometry in the cavity 24.

The magnitude of the radius of expansion (and thus diameter D3) depends upon the relative increase in diameter in the region 22 brought about by exposure to heat and interior pressure within the cavity 24. The relative increase between the extruded or molded tube diameter D1 and diameter D3 should be at least 5% to provide tube length and geometry of the segment when it expands beyond diameter D3.

Figure 4B:
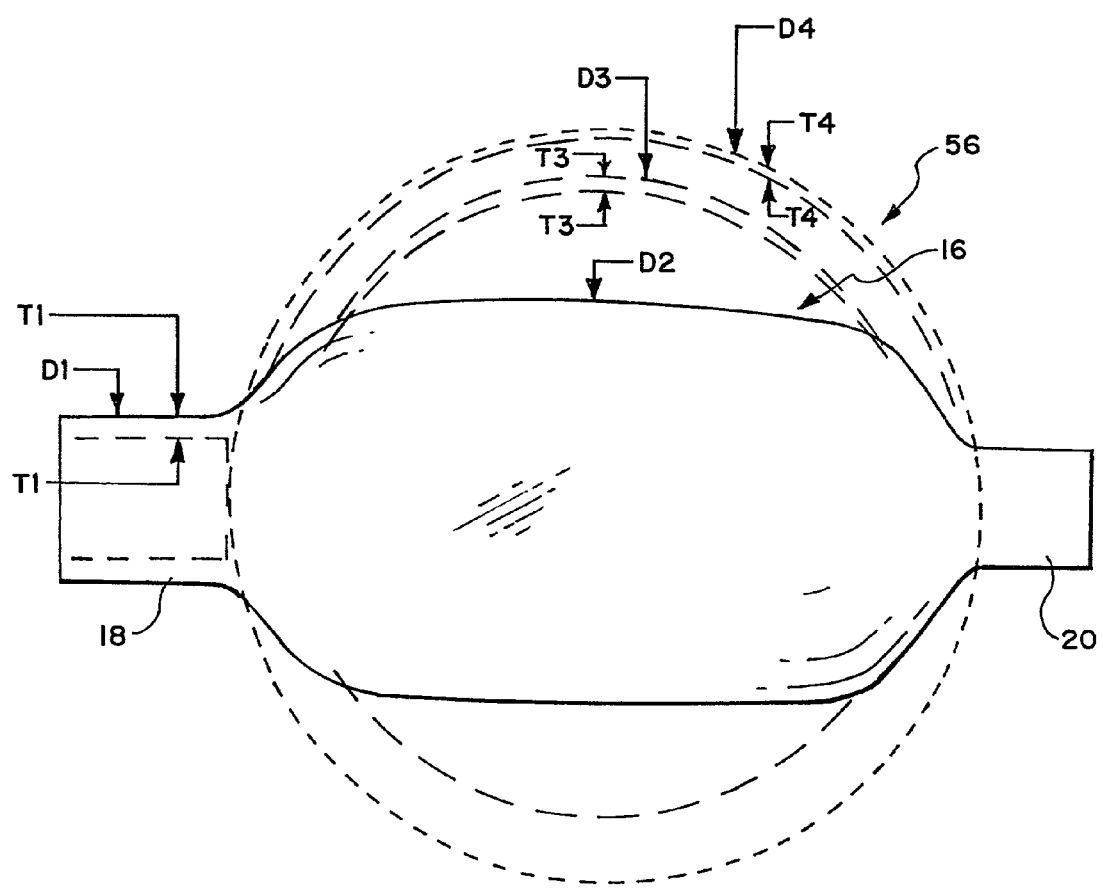

As FIG. 4B shows, due to expansion of heat-softened material under pressure in the cavity 24, the wall thickness of the structure 56 is not uniform. The region 22 has a minimum wall thickness T3 when in its normally enlarged diameter D3, which is less than the normal extruded or molded wall thickness (T1) of the tube 16.

Continued volume flow of pressurized fluid into the structure 56 at the threshold pressure P(t) continues to increase the interior volume of the structure 56. As its volume increases, the shaped region 22 of the structure 56 continues to enlarge beyond the normal diameter D3 toward a distended shape and geometry, designated D4 in FIG. 4. The threshold pressure P(t) stays generally constant as volume increases between D3 and D4. As long as volume is controlled (i.e., so as not to substantially exceed D4), there is no need for an external pressure regulator. Volume expansion between D3 and D4 at a substantially constant pressure occurs because of the material properties of the structure 56, and not because of some external pressure control mechanism.

Enlargement of the structure in the region between D3 and D4 stretches the material in the region 22 beyond its stress-relieved condition. Consequently, the wall thickness T4 at the distended geometry D4 is less than the minimum wall thickness T3 of the normally enlarged diameter D3. However, the distended geometry generally maintains the preformed shape dictated by the cavity 24 (which, in the illustrated embodiment, is spherical).

In the expansion region between D3 and D4, the addition of fluid volume at substantially constant P(t) stretches the material, causing the radius of the structure 56 to increase and the wall thickness to decrease. Material stress will increase.

Figure 10:
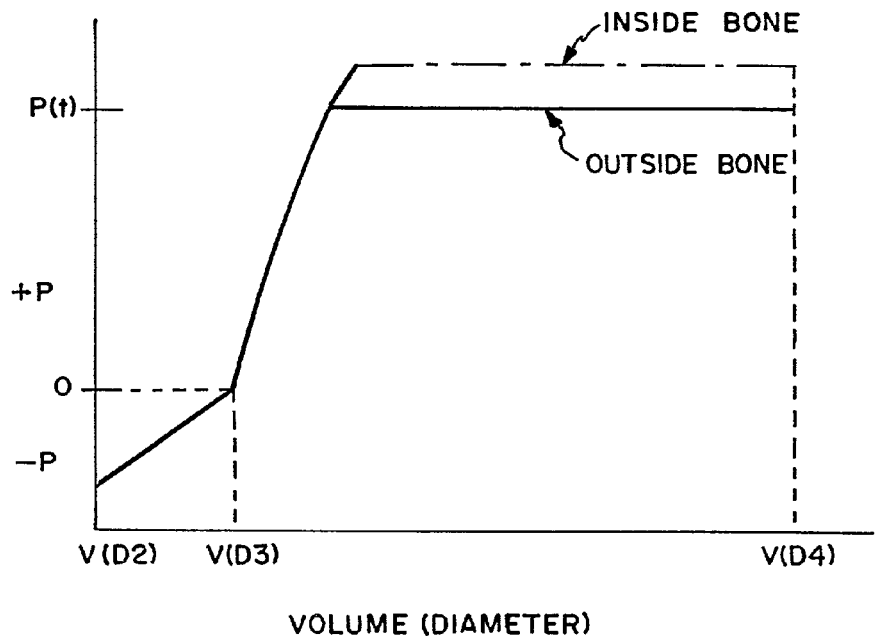
FIG. 10 is a graph which plots the effects of increasing pressure applied to the interior of the structure to the expanded volume of the structure.

While expanding in the region between D3 and D4, the structure 56, when inside bone, assumes an increasingly larger surface and volume, thereby compacting surrounding cancellous bone. Inflation in cancellous bone may occur at the same threshold pressure P(t) as outside bone. However, an increase in the threshold inflation pressure P(t) inside bone may be required, due to the density of the cancellous bone and resistance of the cancellous bone to compaction. In this instance, the configuration of the Pressure vs. Volume curve for a given material and structure 56 remains essentially the same as shown in FIG. 10, except that the generally horizontal portion of the curve between D3 and D4 is shifted upward on the Y-axis, as shown in phantom lines in FIG. 10. As a general statement, the threshold pressure inside bone is determined by the material property of the structure 56 and any added resistance due to the presence of cancellous bone.

The distance between D3 and D4, along the x-axis of FIG. 10, defines the degree to which the wall can elongate at a substantially constant pressure condition and with increasing material stress to compact cancellous bone, without failure. As volume increases at the substantially constant threshold pressure P(t), wall failure becomes more likely as the diameter of the structure enlarges significantly further beyond the distended diameter D4. There comes a point when the structure 56 can no longer increase its volume as the material elasticity approaches ultimate elongation, or as material stress approaches ultimate tensile strength. When either of these ultimate values are reached, wall failure is likely.

The distance between D3 and D4 in FIG. 10 during expansion inside bone is a simultaneous expression of the three physical and mechanical properties—expansion, shape, and toughness—described above. For example, a material possessing the requisite elasticity and shape, but lacking requisite toughness, but may fail short of the shape D4 due to abrasion and tearing caused by cancellous bone.

2. Complex Preformed Expandable Structures

Sometimes it can be difficult to achieve a desired uniformity and area of compaction within a given cancellous bone region using a expandable body 56 having a single expandable region 22, such as shown in FIG. 4.

Figure 12:
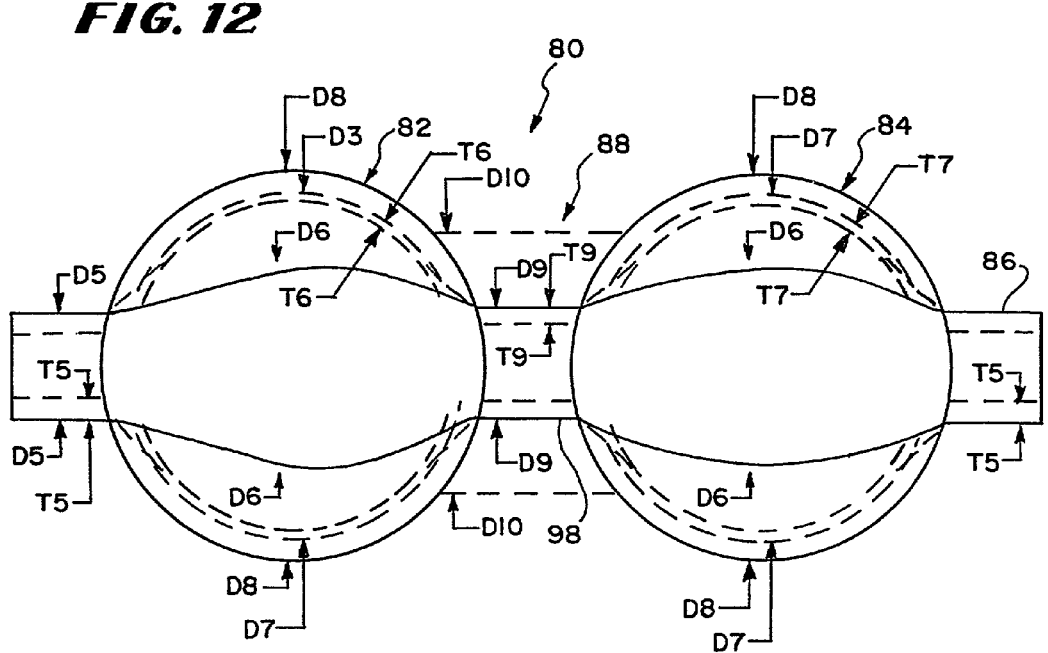
FIG. 12 is a side view of a complex structure which includes several expandable segments spaced along its length.

FIG. 12 shows a complex preformed structure 80 includes segmented expandable regions 82 and 84 spaced along its length. The structure 80 provides a longer profile along which volume can be increased.

The complex expandable structure 80 is created by extruding or molding a tube 86 of polyurethane or elastomer material, like the tube 16 shown in FIG. 5. In the preferred embodiment, the tube 86 is made of a polyurethane material. The tube has a normal extruded wall thickness (T5) and a normal extruded outside diameter (D5) (as shown in FIG. 12).

Figure 13:
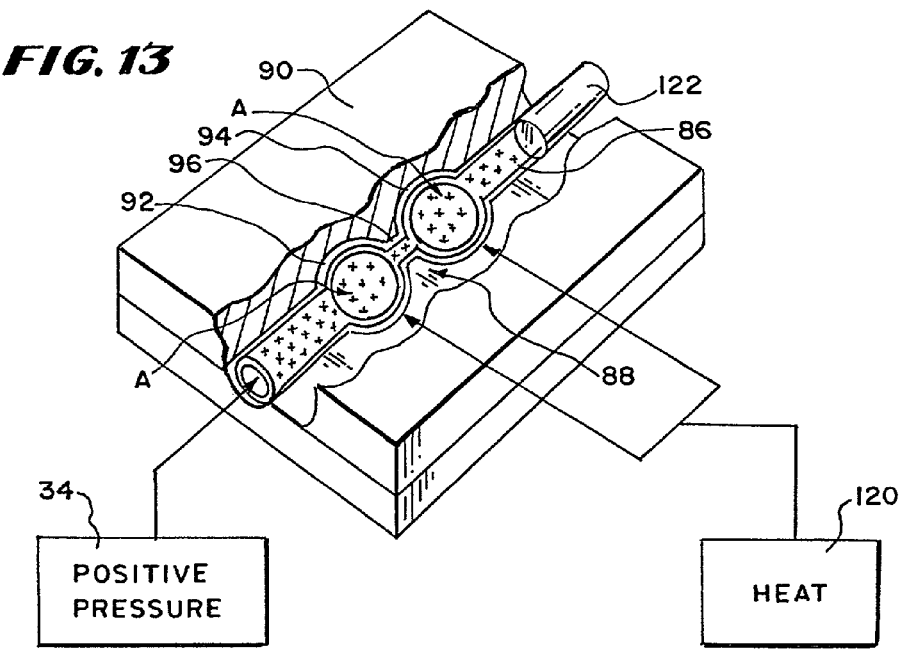
FIG. 13 is a top perspective view of a shape-forming fixture used to apply pressure and heat to an extruded or molded tube to create the structure shown in FIG. 12.

The segmented shaped regions 82 and 84 are created by exposing an intermediate region 88 of the tube 86 to heat and positive interior pressure inside a fixture or mold 90, as shown in FIG. 13. In the illustrated embodiment, the fixture 90 possesses two cavity regions 92 and 94 with an intermediate channel 96. The intermediate region 88 is located in the cavities 92 and 94 and channel 96.

The cavity regions 92 and 94 and the channel 96 are exposed to a source of heat 120, to soften the material of the region 88. When heat-softened (in the manner previously described), the interior of the tube 86 is subjected to positive pressure from a source 34 (as also previously described). The material in the region 88 expands or extends within the cavities 92 and 94 and the channel 96. Once cooled and removed from the fixture 90, the structure 80 can be attached to the distal end of a catheter tube 50 in the same fashion as the structure 56 shown in FIGS. 3 and 4.

The structure 80 possesses, in an open air environment, a normal expanded shape, having diameter D7 (shown in phantom lines in FIG. 12). The normal shape and diameter D7 for the regions 82 and 84 generally correspond with the shape and dimension of the cavities 92 and 94, respectively.

When an interior vacuum is drawn, removing air from the structure 80, the structure 80 assumes a substantially collapsed, and not inflated geometry, shown in phantom lines D6 in FIG. 12. Due to the application of heat and pressure upon the region 88, diameter D6 for each region 82 and 84 is larger than the normal extruded or molded outside diameter D5 of the original extruded tube 86.

The regions 82 and 84 are separated by a tubular neck 98, which segments the structure 80 into two expandable regions 82 and 84. When substantially collapsed under vacuum or not inflated, the structure 80 exhibits a low profile, ideal for insertion into the targeted cancellous bone region.

The introduction of fluid volume back into the tube 86 will cause each region 82 and 84 to return from the collapsed diameter D6 back to the normal, enlarged, but not distended geometry, having the shape and diameter shown in phantom lines D7 in FIG. 12.

In the illustrated embodiment, the first and second shaped regions 82 and 84 have generally the same radius of expansion and thus the same non-distended shape and diameter D7. Alternatively, each region 82 and 84 can have a different radius of expansion, and thus a different non-distended shape and diameter. Regardless, when in the normal, non-distended diameter D7, the material of the structure 80 in the region 88 is not significantly stretched or stressed, because the regions 82 and 84 have been previously expanded in a stress-relieved condition into this geometry in the cavities 92 and 94.

As before explained in conjunction with the structure 56, the regions 82 and 84 can be shaped by heat and interior pressure within different cavities to assume different geometries, e.g., cylindrical or elliptical geometry, or a non-spherical, non-cylindrical, or non-elliptical geometry, with either uniform or complex curvature, and in either symmetric or asymmetric forms. Of course, more than two segmented regions 82 and 84 can be formed along the length of the tube 86.

Each shaped region 82 and 84 possesses a minimum wall thickness (designed T7 in FIG. 12) when in the normally enlarged but not distended geometry D7. Due to expansion of heat-softened material under pressure in the cavities 92 and 94, the wall thickness is not uniform, i.e., T7 is less than the normal extruded or molded wall thickness T5 of the tube 86. The minimum wall thicknesses T7 for the regions 82 and 84 can be the same or different.

When in the enlarged, but not distended geometry, the neck region 98 has an outside diameter (designated D9 in FIG. 14), which is equal to or greater than the normal extruded or molded diameter D5 of the tube 86. The size of the channel 96 in the fixture 90 determines the magnitude of the diameter D9. Due to expansion of heat-softened material in the adjacent regions 82 and 84 under pressure in the cavities 92 and 94, the neck region 98 (which expands under pressure in the channel 96) has a wall thickness (designated T9 in FIG. 12) which is less than or equal to the normal extruded or molded wall thickness T5 of the tube 86, but still greater than the minimum wall thickness T7 of either fully shaped region 82 or 84.

The formed complex structure 80 thus possesses regions of non-uniform minimum wall thickness along its length; that is, $T5 \geq T9 > T7$. The formed complex structure 80 also provides multiple expandable regions 82 and 84 of the same or different enlarged outside diameters (D7), segmented by a neck region 98, in which D6>D5; D7>D6; and D7>D9.

By continuing to apply fluid volume at a constant pressure at a threshold amount P(t), and thereby increasing the volume within the structure 80, the shaped regions 82 and 84 of the structure 80 will continue to enlarge beyond diameter D7 to a distended shape and geometry, designated D8 in FIG. 12. The wall thickness T7 further decreases and approaches T8. As the regions 82 and 84 approach diameter D8, the diameter D9 of the neck region 98 will likewise increase toward diameter D10, as FIG. 12 shows, providing more uniform, elongated surface contact with cancellous bone.

Enlargement of the structure 80 beyond diameter D7 stretches the material in the regions 82, 84, and 98 beyond their stress-relieved condition, although the distended geometry of the regions 82 and 84 will, in important respects, maintain the preformed shape dictated by the cavities 92 and 94. As before explained in conjunction with the structure 56, the material in the regions 82 and 84 has already been stress-relieved in the desired shape at the normal diameter D7. As previously explained, enlargement toward the distended diameter D8 occurs at substantially constant pressure (as FIG. 10 exemplifies), and at increasing material stress.

The degree of stretching at a substantially constant incremental pressure condition can be tailored to achieve a desired, fully distended diameter D8. The final, fully distended diameter D8 can be selected to match the dimensions of the targeted cancellous bone region. The controlled stretching of the segmented regions 82 and 84 in tandem can provide an equal volume compression of cancellous bone with a major diameter that is less than a single non-segmented region (i.e., one without the neck region 98). Stated another way, segmented regions 82 and 84, when expanded to a given inflation volume, have a diameter less than a sphere expanded to an equal inflation volume.

While expanding in the region between D7 and D8, the structure 80, like the structure 56, when inside bone, assumes an increasingly larger surface and volume, thereby compacting surrounding cancellous bone. Inflation in cancellous bone may occur at the same threshold pressure P(t) as outside bone. However, an increase in the threshold inflation pressure P(t) inside bone may be required, due to the density of the cancellous bone and resistance of the cancellous bone to compaction.

3. Composite Expandable Structures

Figure 16:
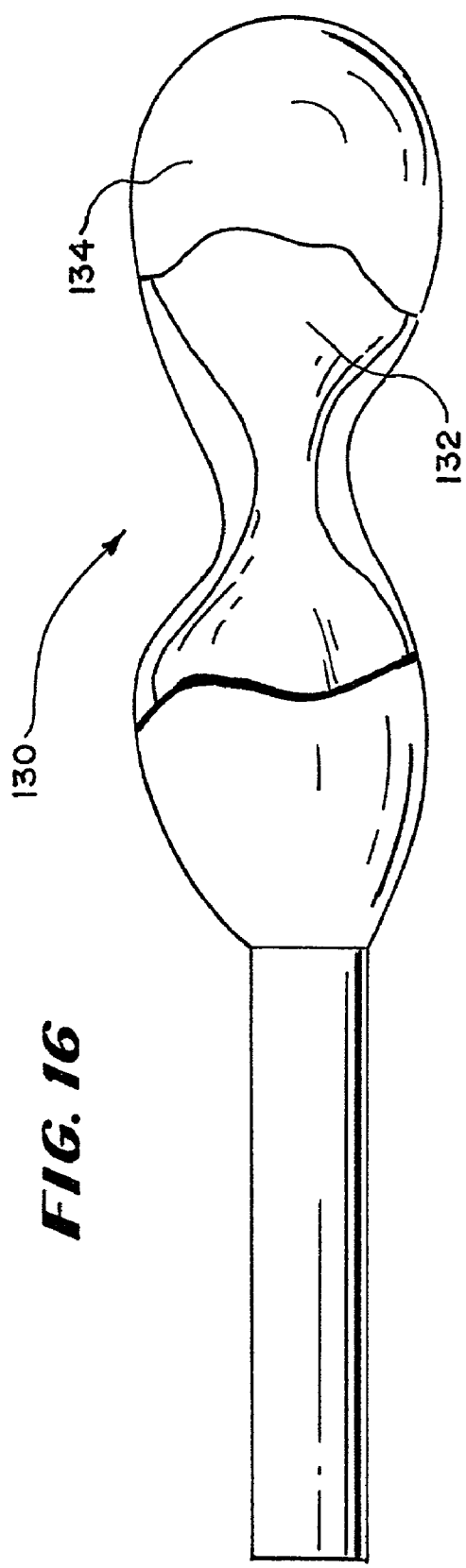
FIG. 16 is a side view, partly in section, of a composite expandable structure.

In the previous embodiments, the material of the structure 56 or 80 is selected to integrate all desired physical and mechanical requirements of expansion, shape, and toughness. FIG. 16 exemplifies a composite expandable structure 130, in which the desired physical and mechanical requirements are segregated by the use of different materials.

As shown in FIG. 16, the composite structure 130 includes an inner expandable body 132 made of a first material that meets one or more of the desired requirements of expansion and shape. The composite structure 130 includes an outer expandable body or shell 134, which is made of a second material that meets the desired requirement of toughness. The shell 134 encapsulates and protects the inner expandable body 132 from surface abrasion, tearing, or puncture due to contact with cancellous bone.

The shell 134 can comprise a material applied to the surface of the inner body by various dipping, painting, or coating techniques. Alternatively, the shell 134 can comprise a bag or sock, into which the inner body 132 is placed prior to deployment. The material for the shell 134 can comprise, e.g., rubber, silicone, ethylene vinyl acetate, polyurethane, polyethylene, or multi-filament woven material or fabric or other polymer material.

The composite structure 130 makes it possible to isolate the expansion and shape requirements from the toughness requirement. A material completely or partially failing to meet the toughness requirement can nevertheless be used for the inner body 132 to optimize the expansion and shape requirements of the structure 130. The inner body 132 imparts its optimized expansion and shape characteristics to cancellous bone, while the shell 134 imparts its optimized toughness characteristic to the overall composite structure 130.

II. Deployment of Preformed Expandable Structures in Bone

Figure 8:
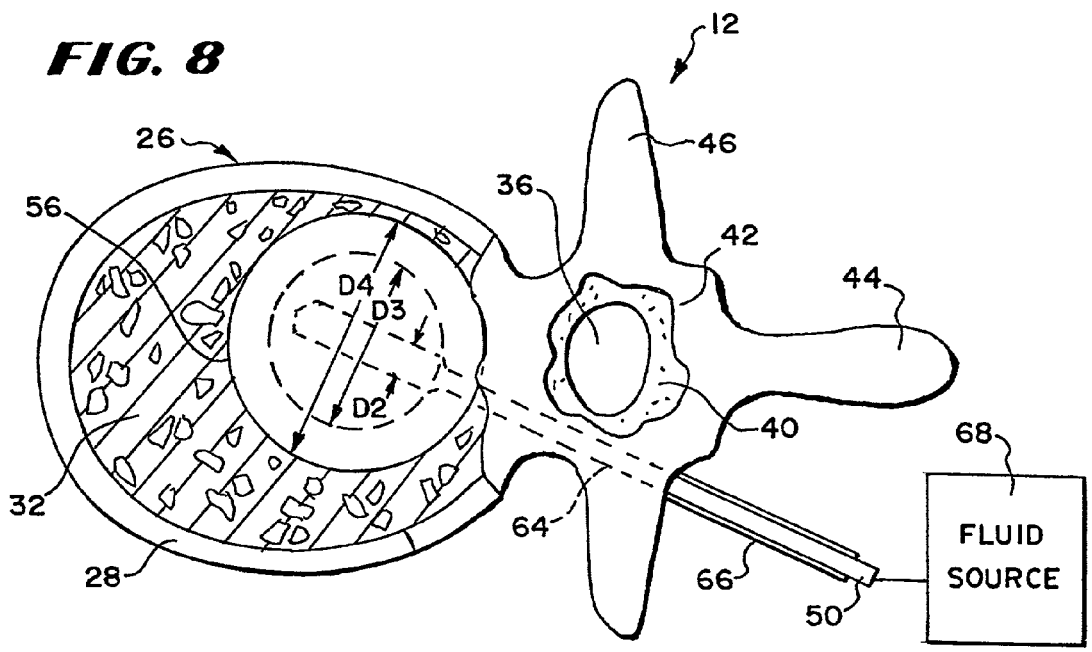
FIG. 8 is a coronal view of the vertebral body shown in FIG. 1, with the tool shown in FIG. 3 deployed to compress cancellous bone as a result of inflating the expandable structure.

The structure 56 or 80 or 130 can be inserted into bone in accordance with the teachings of U.S. Pat. Nos. 4,969,888 and 5,108,404, which are incorporated herein by reference. As FIG. 8 shows, access can be accomplished, for example, by drilling an access portal 64 through a side of the vertebral body 26. This is called a postero-lateral approach. Alternatively, the access portal can pass through either pedicle 42, which called a transpedicular approach.

A guide sheath or cannula 66 is placed into communication with the access portal 64. The catheter tube 50 is advanced through the cannula 66 to deploy the structure (FIG. 8 shows structure 56) into contact with cancellous bone 32. The structure 56 is in its normally collapsed and not inflated condition (shown as phantom line diameter D2 in FIG. 8) during deployment. Access in this fashion can be accomplished using a closed, minimally invasive procedure or with an open procedure.

The materials for the catheter tube 50 are selected to facilitate advancement of the expandable structure 56 into cancellous bone 32. The catheter tube 50 can be constructed, for example, using standard flexible, medical grade plastic materials, like vinyl, nylon, polyethylenes, ionomer, polyurethane, and polyethylene tetraphthalate (PET). The catheter tube 50 can also include more rigid materials to impart greater stiffness and thereby aid in its manipulation. More rigid materials that can be used for this purpose include stainless steel, nickel-titanium alloys (Nitinol™ material), and other metal alloys.

Figure 9:
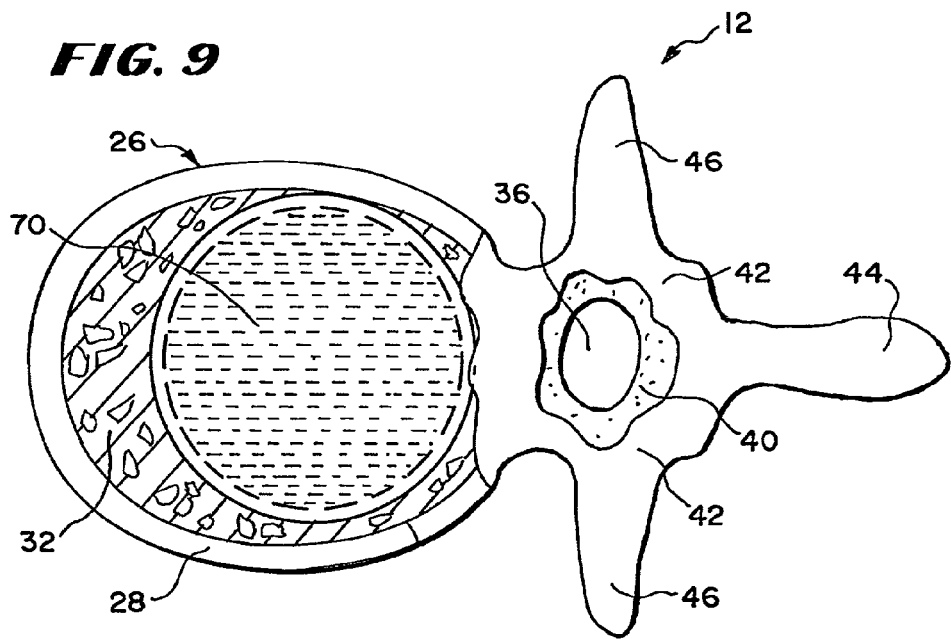
FIG. 9 is a coronal view of the vertebral body shown in FIG. 8, upon removal of the tool, showing the cavity formed by the compression of cancellous bone by the expandable structure.

As FIG. 8 shows, expansion of the structure 56 to its enlarged but not distended geometry (phantom line diameter D3 in FIG. 8), and ultimately to its maximum distended geometry (diameter D4 in FIG. 8) sequentially compresses cancellous bone 32 in the vertebral body 26. The compression forms an interior cavity 70 in the cancellous bone 32. As FIG. 9 shows, subsequent collapse and removal of the structure 56 leaves the cavity 70 in a condition to receive a filling material, e.g., bone cement. The bone cement, when hardened, provides improved interior structural support for cortical bone 32.

The compaction of cancellous bone 32 shown in FIG. 8 also exerts interior force upon the surrounding cortical bone 28. The interior force can elevate or push broken and compressed bone back to or near its original prefracture, or other desired, condition.

In the case of a vertebral body 26, deterioration of cancellous bone 32 can cause the top and bottom plates (designated TP and BP in FIG. 2) to compress or move closed together, reducing the normal physiological height between the plates TP and BP. In this circumstance, the interior force exerted by the structure 56 as it compacts cancellous bone 32 moves one or both of the top and bottom plates TP and BP farther apart, to thereby restore a spacing between them, which is at or close to the normal physiological distance.

Figure 11:
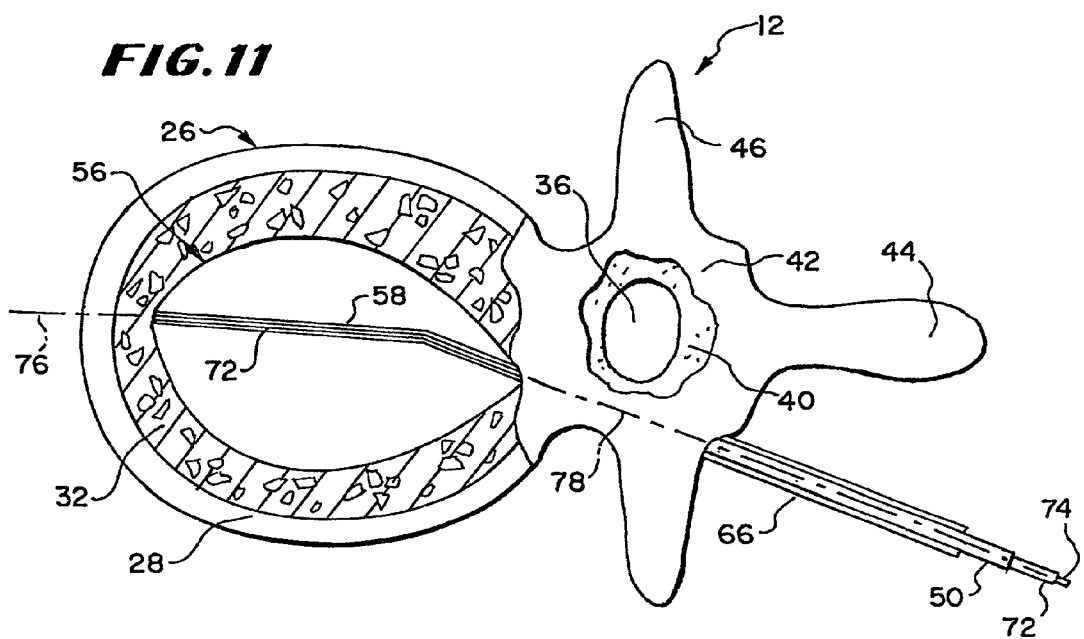
FIG. 11 is a coronal view of the vertebral body shown in FIG. 8, with the tool deployed to compress cancellous bone, and in which a bendable stylet alters the orientation of the expandable structure in cancellous bone.

As shown in FIG. 11, in an alternative embodiment, a stiffening member or stylet 74 can be inserted through a lumen 72 of the auxiliary tube 58, which is enclosed within the structure 56. The stylet 74 can be made, e.g., from stainless steel or molded plastic material. The presence of the stylet 74 serves to keep the structure 56 in the desired distally straightened condition during passage through the guide sheath 66 into the targeted bone region, as FIG. 8 shows.

As further shown in FIG. 11, the stylet 74 can have a preformed memory, to normally bend its distal region. The memory is overcome to straighten the stylet 14 when confined within the guide sheath 66. However, as the structure 56 and preformed stylet 74 advance free of the guide sheath 66 and pass into the targeted region, the preformed memory bends the stylet 74. The bending stylet 74 bends the auxiliary tube 58 and thereby shifts the main axis 76 of the surrounding expandable structure 56 relative to the axis 78 of the access path (i.e., the guide sheath 66). The prebent stylet 74, positioned within the interior of the structure 56, aids in altering the orientation of the structure 56 within targeted region. It is thereby possible to orient the structure 56 in a more generally aligned relationship with the natural axes of the vertebral body 26. A cavity 70, more centrally located within the bone, e.g., a vertebral body 26, can be established, which provides more uniform support across the mid region of the vertebral body 26 when filled with bone cement. The capability of the vertebral body 26 to withstand loads is thereby enhanced. The symmetric compaction of cancellous bone 32 in the interior volume also exerts more equal and uniform interior forces upon cortical bone 32, to elevate or push broken and compressed bone.

There are times when a lesser amount of cancellous bone compaction is indicated. For example, when the bone disease being treated is localized, such as in avascular necrosis, or where local loss of blood supply is killing bone in a limited area, an expandable structure 56 or 80 or 130 can compact a smaller volume of total bone. This is because the diseased area requiring treatment is smaller.

Another exception lies in the use of an expandable structure 56 or 80 or 130 to improve insertion of solid materials in defined shapes, like hydroxyapatite and components in total joint replacement. In these cases, the structure shape and size is defined by the shape and size of the material being inserted.

Yet another exception lies in the use of expandable structures in bones to create cavities to aid in the delivery of therapeutic substances, as disclosed in copending U.S. patent application Ser. No. 08/485,394, previously mentioned. In this case, the cancellous bone may or may not be diseased or adversely affected. Healthy cancellous bone can be sacrificed by significant compaction to improve the delivery of a drug or growth factor which has an important therapeutic purpose. In this application, the size of the expandable structure 56 or 80 or 130 is chosen by the desired amount of therapeutic substance sought to be delivered. In this case, the bone with the drug inside may need to be supported by standard methods while the drug works and the bone heals.

III. Single Use

Distention of any one of the expandable structures 56 or 80 or 130 described herein during first use in a targeted body region generates stress on the material or materials which make up the structure. The material stress created by operational loads during first use in a targeted body region can significantly alter the preformed morphology of the structure, making future performance of the structure unpredictable.

For example, expansion within bone during a single use creates contact with surrounding cortical and cancellous bone. Regardless of the superior mechanical properties of material, this contact can in time damage the structure, creating localized regions of weakness, which may escape detection. Localized areas of lower density cancellous bone may result in creating areas of differential expansion and stress on the structure. The existence of localized regions of weakness or differential stress can unpredictably cause overall structural failure during a subsequent use.

In addition, exposure to blood and tissue during a single use can entrap biological components on or within the structure or the associated catheter tube. Despite cleaning and subsequent sterilization, the presence of entrapped biological components can lead to unacceptable pyrogenic reactions.

As a result, following first use, the structure can not be consistently relied upon to reach its desired configuration during subsequent use and may not otherwise meet established performance and sterilization specifications. The effects of material stress and damage caused during a single use, coupled with the possibility of pyrogen reactions even after resterilization, reasonably justify imposing a single use restriction upon devices which carry these expandable structures for deployment in bone.

Figure 14:
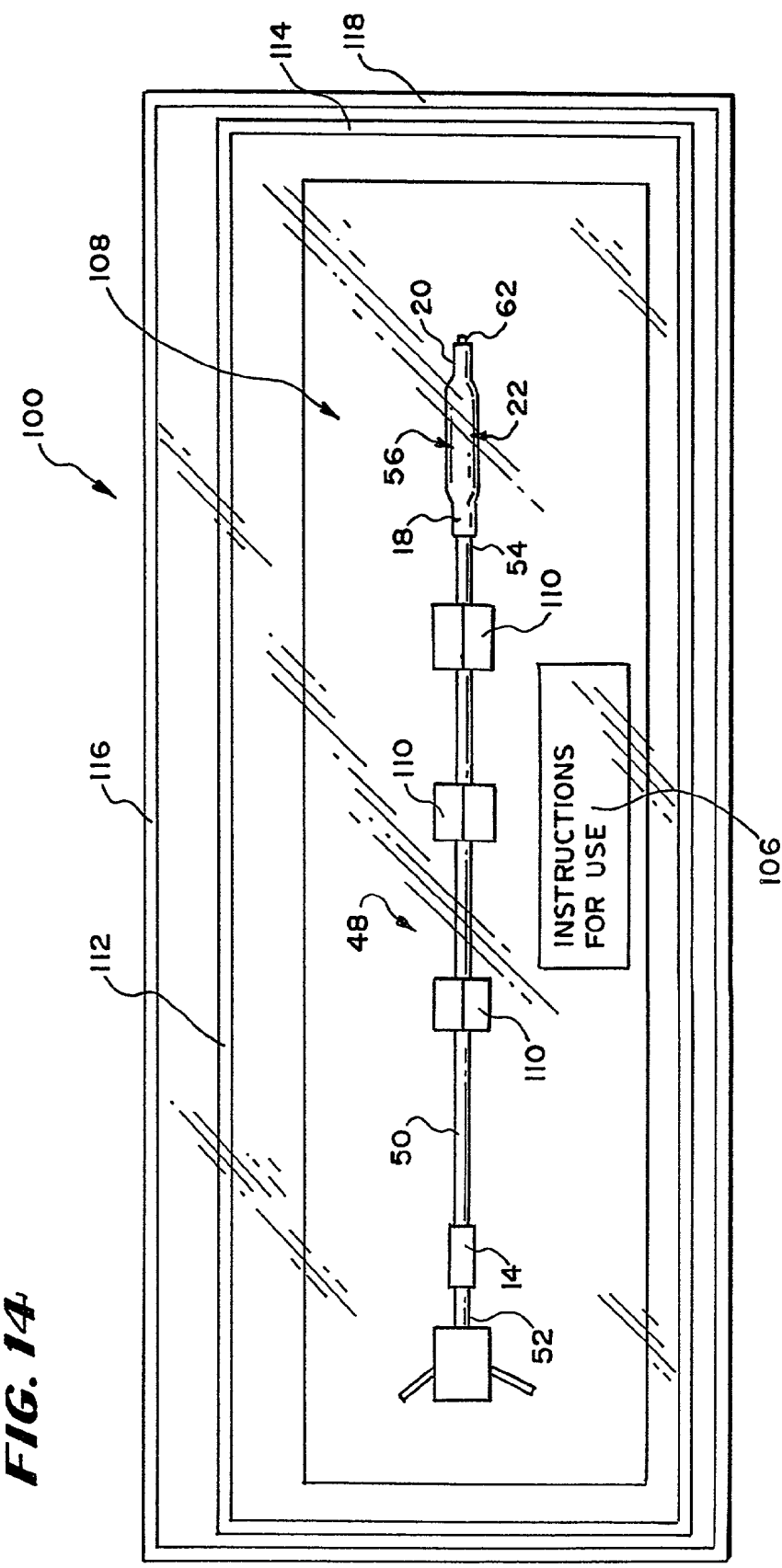
FIG. 14 is a top view of a kit which holds the tool shown in FIG. 3 in a sealed, sterile environment prior to use.
Figure 15:
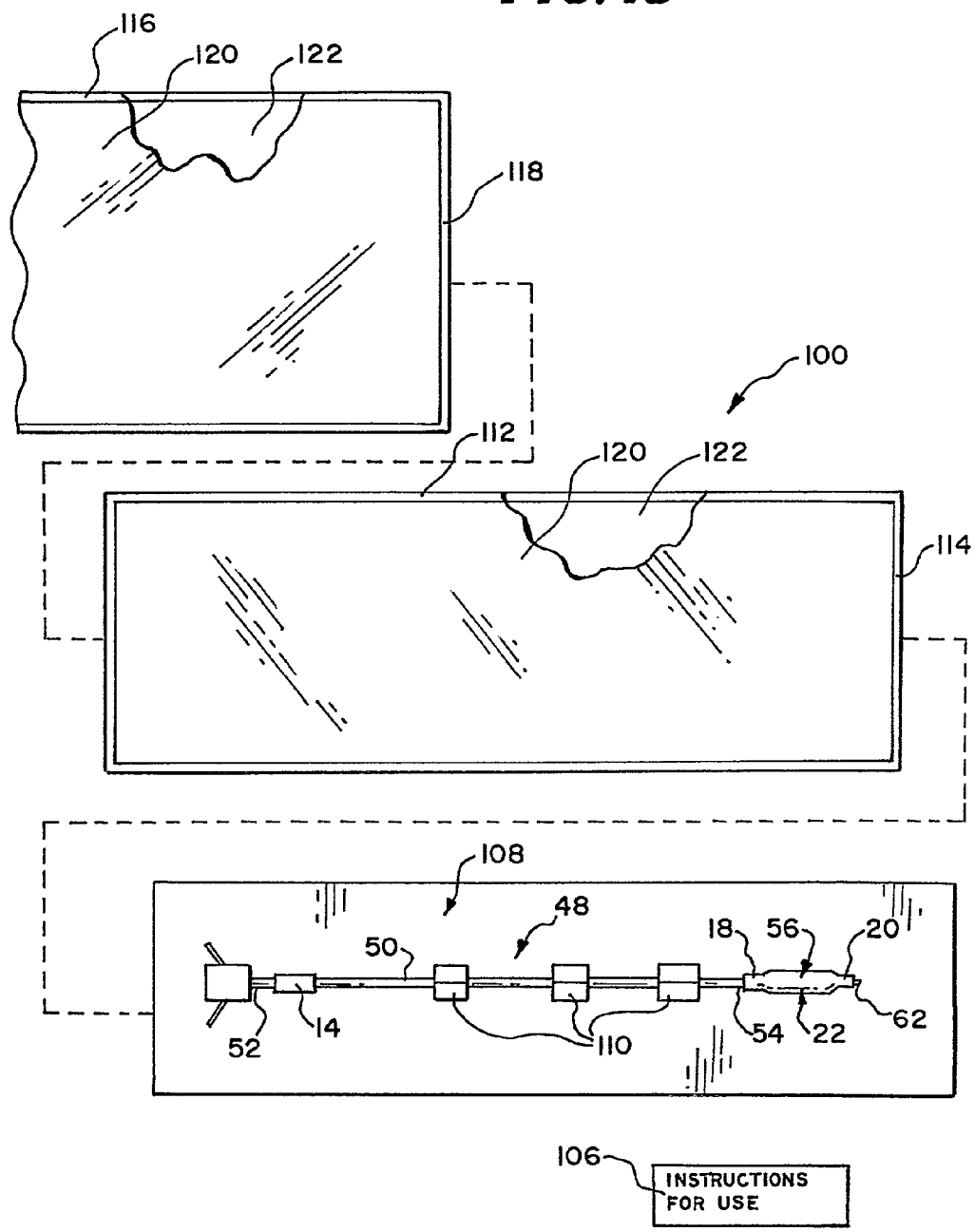
FIG. 15 is an exploded view of the kit shown in FIG. 14.

To protect patients from the potential adverse consequences occasioned by multiple use, which include disease transmission, or material stress and instability, or decreased or unpredictable performance, the invention also provides a kit 100 (see FIGS. 14 and 15) for storing a single use tool 48 (also shown in FIG. 3) prior to use. As shown in FIG. 14, the tool 48 carries an expandable structure. FIG. 14 shows for the purpose of illustration the structure 56, as described herein. It should be appreciated that the tool 48 could carry an expandable structure 80 or 130, as also previously described.

In the illustrated embodiment (see FIGS. 14 and 15), the kit 100 includes an interior tray 108. The tray 108 holds the tool 48 in a lay-flat, straightened condition during sterilization and storage prior to its first use. The tray 108 can be formed from die cut cardboard or thermoformed plastic material. The tray 108 includes one or more spaced apart tabs 110, which hold the catheter tube 50 and expandable structure 56 in the desired lay-flat, straightened condition.

The kit 100 includes an inner wrap 112, which is peripherally sealed by heat or the like, to enclose the tray 108 from contact with the outside environment. One end of the inner wrap 112 includes a conventional peal-away seal 114, to provide quick access to the tray 108 upon instance of use, which preferably occurs in a sterile environment, such as within an operating room.

The kit 100 also includes an outer wrap 116, which is also peripherally sealed by heat or the like, to enclosed the inner wrap 112. One end of the outer wrap 116 includes a conventional peal-away seal 118, to provide access to the inner wrap 112, which can be removed from the outer wrap 116 in anticipation of imminent use of the probe 102, without compromising sterility of the probe 102 itself.

Both inner and outer wraps 112 and 116 (see FIG. 15) each includes a peripherally sealed top sheet 120 and bottom sheet 122. In the illustrated embodiment, the top sheet 120 is made of transparent plastic film, like polyethylene or MYLAR™ material, to allow visual identification of the contents of the kit 100. The bottom sheet 122 is made from a material that is permeable to ETO sterilization gas, e.g., TYVEK™ plastic material (available from DuPont).

The sterile kit 100 also carries a label or insert 106, which includes the statement "For Single Patient Use Only" (or comparable language) to affirmatively caution against reuse of the contents of the kit 100. The label 106 also preferably affirmatively instructs against resterilization of the tool 48. The label 106 also preferably instructs the physician or user to dispose of the tool 48 and the entire contents of the kit 100 upon use in accordance with applicable biological waste procedures. The presence of the probe 102 packaged in the kit 100 verifies to the physician or user that tool 48 is sterile and has not been subjected to prior use. The physician or user is thereby assured that the expandable structure 56 meets established performance and sterility specifications, and will have the desired configuration when expanded for use.

The label 106 preferably also instructs the physician as to the use of the expandable structure 56 (or 80 or 130) for compacting cancellous bone in the manners previously described. For example, the label 106 instructs the physician to expand the structure inside bone to compact cancellous bone and form a cavity. The label 106 can also instruct the physician to fill the cavity with a material, e.g., bone cement, allograft material, synthetic bone substitute, a medication, or a flowable material that sets to a hardened condition.

The features of the invention are set forth in the following claims.

We claim:
1. A device comprising
a wall made from a flexible material resistant to abrasion by cancellous bone,
the wall peripherally defining an interior space and including an expandable region preformed with a normally expanded shape outside bone, the expandable region being expandable beyond its normally expanded shape to reach an inflation volume sized and configured for compacting cancellous bone,
the expandable region having proximal and distal ends,
the expandable region further having a first expanded section having an interior cross-sectional area adjacent the proximal end, a second expanded section having an interior cross-sectional area adjacent the distal end, and a third section having an interior cross-sectional area located between the first and second expanded sections,
when in the normally expanded shape and at the inflation volume, the interior cross-sectional area of the third section being less than the interior cross-sectional area of either the first or second expanded sections, and
the first expanded section, the second expanded section, and the third expanded section further having, respectively, a first preformed average wall thickness, a second preformed average wall thickness, and a third preformed average wall thickness, and
when in the normally expanded shape and at the inflation volume, the third average wall thickness being greater than either the first average wall thickness or the second average wall thickness.
2. A device according to claim 1
wherein the expandable region, when expanded beyond its normally expanded shape to reach a given inflation volume, presents a maximum diameter less than a sphere expanded to an equal inflation volume.

3. A device according to claim 1
wherein the expandable region includes a further expanded shape, outside bone, having a diameter greater than the normally expanded shape.

4. A device according to claim 3
wherein the expandable region has a further expanded shape inside bone that substantially corresponds to the further expanded shape outside bone.

5. A device according to claim 1
wherein the expandable region is essentially cylindrical.

6. A device according to claim 1
wherein the expandable region expands in a non-spherical manner.

7. A device according to claim 1
wherein the expandable region expands in an essentially cylindrical manner.

8. A device according to claim 1
wherein the expandable region is preformed by the application of heat and pressure.

9. A device comprising
an expandable structure preformed with a normally expanded shape and being expandable beyond its normally expanded shape to a reach an inflation volume sized and configured for manipulating bone, the structure having a wall material peripherally defining an interior space, the wall material being resistant to abrasion by cancellous bone,
the structure having a proximal and a distal end,
the structure further having a first expandable region located near the distal end and a second expandable region located proximally of the first expandable region, the first and second expandable regions separated by a third region of the structure, the third region having a reduced cross-sectional area as compared to the cross-sectional areas of the first and second regions when the structure is in the normal expanded shape and at the inflation volume, and
the first expandable region, the second expandable region, and the third expandable region further having, respectively, a first preformed average wall thickness, a second preformed average wall thickness, and a third preformed average wall thickness, and
the third average wall thickness being greater than either the first average wall thickness or the second average wall thickness when the structure is in the normal expanded shape and at the inflation volume.

10. A device according to claim 9
wherein the wall material of the first expandable region substantially surrounds a first maximum cross-sectional area of the interior space, the wall material of the second expandable region substantially surrounds a second maximum cross-sectional area of the interior space, and the wall material of the third region substantially surrounds a minimum cross-sectional area of the interior space, the first and second maximum cross-sectional areas each being larger than the minimum cross-sectional area.

11. A device according to claim 9 wherein the wall material comprises polyurethane.

12. A device according to claim 9
wherein the expandable structure is preformed by the application of heat and pressure.

13. A device comprising
a wall made from a flexible material resistant to abrasion by cancellous bone, the wall peripherally defining an interior space and including an expandable region preformed with a normally expanded shape and being expandable beyond its normally expanded shape to a reach an inflation volume sized and configured for compacting cancellous bone,
the expandable region having proximal and distal ends,
the expandable region further having a first expanded section adjacent the distal end, a second expanded section located proximally of the first expanded section, and a third section located between the first and second expanded sections,
wherein the average outer diameter of the third section is less than the average outer diameter of either of the first or second expanded sections when the structure is in the normal expanded shape and at the inflation volume, and
the first expandable section, the second expandable section, and the third expandable section further having, respectively, a first preformed average wall thickness, a second preformed average wall thickness, and a third preformed average wall thickness, and
the third average wall thickness being greater than either the first average wall thickness or the second average wall thickness when the structure is in the normal expanded shape and at the inflation volume.

14. A device according to claim 13
wherein the expandable region expands in response to introduction of a flowable material into the interior space.

15. A device according to claim 13
wherein the expandable region is preformed by the application of heat and pressure.

* * * * *

UNITED STATES PATENT AND TRADEMARK OFFICE
CERTIFICATE OF CORRECTION

| | |
|---|---|
| PATENT NO. | : 6,979,341 B2 |
| DATED | : December 27, 2005 |
| INVENTOR(S) | : Robert M. Scribner and Karen D. Talmadge |

It is certified that error appears in the above-identified patent and that said Letters Patent is hereby corrected as shown below:

Title page,
Item [63], Related U.S. Application Data, insert -- US 2004/0267271 A9 Dec. 30, 2004 --.

Column 15,
Line 23, after "shape to" delete "a".

Column 16,
Line 18, after "shaped to" delete "a".

Signed and Sealed this

Eighteenth Day of April, 2006

JON W. DUDAS
*Director of the United States Patent and Trademark Office*